United States Patent [19]

Engel et al.

[11] Patent Number: 4,971,966

[45] Date of Patent: Nov. 20, 1990

[54] SUBSTITUTED PYRIDO(2,3-b) (1,4) BENZODIAZEPIN-6-ONES, AND MEDICAMENTS CONTAINING THESE COMPOUNDS

[75] Inventors: Wolfhard Engel; Wolfgang Eberlein, both of Biberach; Gunter Trummlitz, Warthausen; Gerhard Mihm; Norbert Mayer, both of Biberach, all of Fed. Rep. of Germany; Adriaan de Jonge, Driebergen, Netherlands

[73] Assignee: Karl Thomae GmbH, Biberach an der Riss, Fed. Rep. of Germany

[21] Appl. No.: 80,716

[22] Filed: Jul. 31, 1987

[30] Foreign Application Priority Data

Jul. 31, 1986 [DE] Fed. Rep. of Germany ....... 3626095

[51] Int. Cl.$^5$ .................... A61K 31/55; C07D 471/04
[52] U.S. Cl. .................................... 514/220; 540/495
[58] Field of Search ......................... 540/495; 514/220

[56] References Cited

U.S. PATENT DOCUMENTS 4,550,107  10/1985  Engel et al. .......................... 514/220

Primary Examiner—John M. Ford
Attorney, Agent, or Firm—D. E. Frankhouser; M-E. M. Timbers; A. R. Stempel

[57] ABSTRACT

New substituted pyrido[2,3-b][1,4]benzodiazepin-6-ones suitable as vagal pacemakers for the treatment of bradycardias and bradyarrhythmias in human and veterinary medicine are described.

7 Claims, No Drawings

SUBSTITUTED PYRIDO(2,3-b) (1,4) BENZODIAZEPIN-6-ONES, AND MEDICAMENTS CONTAINING THESE COMPOUNDS

The invention relates to new substituted 6H-pyrido[2,3-b][1,4]benzodiazepin-6-ones, to processes for their preparation and to medicaments containing these compounds.

EP-A-39519 and 57428 and U.S. Pat. Nos. 3,660,380; 3,691,159; 4,213,984; 4,213,985; 4,210,648; 4,410,527; 4,424,225; 4,424,222; and 4,424,226 disclose condensed diazepinones having ulcer inhibiting and gastric-acid secretion inhibiting properties.

EP-A-156191 (U.S. Pat. No. 4,550,107) describes obtaining by introducing novel aminoacyl radicals, valuable pharmacological properties which are different in type from those of the compounds of the above-mentioned publications and patents. Compared with the latter compounds, the substituted pyrido[2,3-b][1,4]benzodiazepin-6-ones according to the invention are surprisingly distinguished by a considerably intensified action and absorption after oral administration, with comparable or improved selectivity.

The new substituted pyrido[2,3-b][1,4]benzodiazepin-6-ones have the general formula I

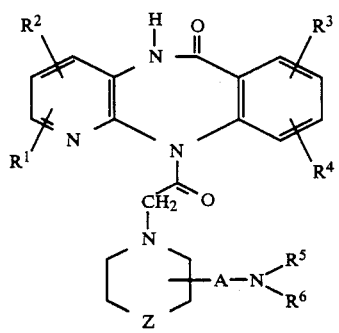

in which
  $R^1$ denotes an alkyl group having 1 to 4 C-atoms, a chlorine atom or a hydrogen atom;
  $R^2$ denotes a hydrogen atom or a methyl group;
  $R^3$ and $R^4$ each denote a hydrogen atom, a fluorine, chlorine or bromine atom, or an alkyl group having 1 to 4 C-atoms, but with the proviso that at least one of the radicals $R^1$, $R^2$, $R^3$ and $R^4$ is different from hydrogen,
and in which
  $R^5$ and $R^6$ are alkyl radicals which are identical or diffrrent from one another and have up to 6 carbon atoms, or form, together with the nitrogen atom between them, a 4- to 7-membered, saturated, monocyclic, heteroaliphatic ring which can optionally be interrupted by an oxygen atom or by the N-CH$_3$ group,
and in which
  Z is either a single bond or an oxygen atom, a methylene or 1,2-ethylene group, and
  A is a methylene group in the 2- or 3-position of the heteroaliphatic ring and, in the case of linkage in the 3-position, is a single bond.

The preferred compounds of the general formula I are those which carry as aminoacyl radical the [[2-[(diethylamino)methyl]-1-piperidinyl]acetyl]radical and are monochloro or monomethyl substituted in the 2-, 8- or 9-position, or are monobromo or monoethyl substituted in the 8- or 9-position.

The compounds of the general formula I can, after reaction with inorganic or organic acids, also exist in the form of their physiologically acceptable salts. Examples of acids which are suitable include hydrochloric, hydrobromic, sulphuric, methylsulphuric, phosphoric, tartaric, fumaric, citric, maleic, succinic, gluconic, malic, p-toluenesulphonic, methanesulphonic or amidosulphonic.

To illustrate the subject-matter of the invention, the following compounds may be mentioned as examples:

2-chloro-11-[[2-[(diethylamino)methyl]-1-piperidinyl]acetyl]-5,11-dihydro-6H-pyrido[2,3-b][1,4]benzodiazepin-6-one 9-chloro-11-[[2-[(diethylamino)methyl]-1-piperidinyl]acetyl]-5,11-dihydro-6H-pyrido[2,3-b][1,4]benzodiazepin-6-one 11-[[2-[(diethylamino)methyl]-1-piperidinyl]acetyl]5,11-dihydro-2-methyl-6H-pyrido[2,3-b][1,4]benzodiazepin-6-one 11-[[2-[(diethylamino)methyl]-1-piperidinyl]acetyl]-5,11-dihydro-8-methyl-6H-pyrido[2,3-b][1,4]benzodiazepin-6-one 11-[[2-[(diethylamino)methyl]-1-piperidinyl]acetyl]-5,11-dihydro-9-methyl-6H-pyrido[2,3-b][1,4]benzodiazepin-6-one 8-chloro-11-[[2-[(diethylamino)methyl]-1-piperidinyl]acetyl]-5,11-dihydro-6H-pyrido[2,3-b][1,4]benzodiazepin-6-one 11-[[2-[(diethylamino)methyl]-1-piperidinyl]acetyl]5,11-dihydro-2,4,10-trimethyl-6H-pyrido[2,3-b][1,4]benzodiazepin-6-one 11-[[2-[(diethylamino)methyl]-1-piperidinyl]acetyl]5,11-dihydro-2,4,8-trimethyl-6H-pyrido[2,3-b][1,4]benzodiazepin-6-one 11-[[2-[(diethylamino)methyl]-1-piperidinyl]acetyl]-5,11-dihydro-2,8-dimethyl-6H-pyrido[2,3-b][1,4]benzodiazepin-6-one 8,10-dichloro-11-[[2-[(diethylamino)methyl]-1-piperidinyl]-acetyl]-5,11-dihydro-6H-Pyrido[2,3-b][1,4]benzodiazepin-6-one 11-[[2-[(diethylamino)methyl]-1-piperidinyl]acetyl]-5,11-dihydro-2,10-dimethyl-6H-pyrido[2,3-b][1,4]benzodiazepin-6-one 11-[[2-[(diethylamino)methyl]-1-piperidinyl]acetyl]5,11-dihydro-2,4-dimethyl-6H-pyrido[2,3-b][1,4]benzodiazepin-6-one 2,9-dichloro-11-[[2-[(diethylamino)methyl]-1-piperidinyl]-acetyl]-5,11-dihydro-6H-pyrido[2,3-b][1,4]benzodiazepin-6-one 2,10-dichloro-11-[[2-[(diethylamino)methyl]-1-piperidinyl]-acetyl]-5,11-dihydro-6H-pyrido[2,3-b][1,4]benzodiazepin-6-one 11-[[2-[(diethylamino)methyl]-1-piperidinyl]acetyl]-5,11-dihydro-10-methyl-6H-pyrido[2,3-b][1,4]benzodiazepin-6-one 10-bromo-11-[[2-[(diethylamino)methyl]-1-piperidinyl]acetyl]-5,11-dihydro-6H-pyrido[2,3-b][1,4]benzodiazepin-6-one 11-[[2-[(diethylamino)methyl]-1-piperidinyl]acetyl]5,11-dihydro-8-fluoro-6H-pyrido[2,3-b][1,4]benzodiazepin-6-one 11-[[2-[(diethylamino)methyl]-1-piperidinyl]acetyl]5,11-dihydro-9-fluoro-6H-pyrido[2,3-b][1,4]benzodiazepin-6-one 11-[[2-[(diethylamino)methyl -1-piperidinyl]acetyl]-5,11-dihydro-7-methyl-6H-pyrido[2,3-b][1,4]benzodiazepin-6-one 11-[[2-[(diethylamino)methyl]-1-piperidinyl]acetyl]-5,11-dihydro-7-fluoro-6H-pyrido[2,3-b][1,4]benzodiazepin-6-one 8-bromo-11-[[2-[(diethylamino)methyl]-1-piperidinyl]acetyl]-5,11-dihydro-6H-pyrido[2,3-b][1,4]benzodiazepin-6-one 11-[[2-[(diethylamino)methyl]-1-piperidinyl]acetyl]-5,11-dihydro-8-ethyl-6H-pyrido[2,3-b][1,4]benzodiazepin-6-one 11-[[2-[(diethylamino)methyl]-1-piperidinyl]acetyl]-5,11-dihydro-8,9-dimethyl-6H-pyrido[2,3-b][1,4]benzodiazepin-6-one (+)-9-chloro-11-[[2-[(diethylamino)methyl]-1-piperidinyl]-acetyl]-5,11-dihydro-6H-pyrido[2,3-b][1,4]benzodiazepin-6-one (-)-9chloro-11-[[2-[(diethylamino)methyl]-1-piperidinyl]-acetyl]-5,11-dihydro-6H-pyrido[2,3-b][1,4]benzodiazepin-6-one 9-chloro-5,11-dihydro-11-[[2-[(dimethylamino)methyl]-1piperidinyl]acetyl]-6H-pyrido[2,3-b][1,4]benzodiazepin6-one 9-chloro-5,11-dihydro-11-[[2-[(1-Pyrrolidinyl)methyl]1-piperidinyl]acetyl 6H-pyrido[2,3-b][1,4]benzodiazepin-6-one 9-chloro-5,11-dihydro-11-[[2-[(4-morpholinyl)methyl])1piperidinyl]acetyl]-6H-pyrido[2,3-b][1,4]benzodiazepin6-one 9-chloro-5,11-dihydro-11-[[2-[(4-methyl-1-piperazinyl)methyl]-1-piperidinyl]acetyl]-6H-pyrido[2,3-b][1,4]benzodiazepin-6-one 9-chloro-11-[[3-[(diethylamino)methyl]-1-piperidinyl]acetyl]-5,11-dihydro-6H-pyrido[2,3-b][1,4]benzodiazepin-6-one (S)-9-chloro-11-[[2-[(diethylamino)methyl]-1-pyrrolidinyl]-acetyl]-5,11-dihydro-6H-pyrido[2,3-b][1,4]benzodiazepin-6-one 9-chloro-5,11-dihydro-11-[[3-(dimethylamino)-1-piperidinyl]-acetyl]-6H-pyrido[2,3-b][1,4]benzodiazepin-6-one D,L-9-chloro-11-[[3-[(diethylamino)methyl]-4-morpholinyl]-acetyl]-5,11-dihydro-6H-pyrido[2,3-b][1,4]benzodiazepin-6-one 9-chloro-5,11-dihydro-11-[[2-[(ethylmethylamino)methyl]hexahydro-1H-azepin-1-yl]acetyl]-6H-pyrido[2,3b][1,4]benzodiazepin-6-one 5,11-dihydro-9-methyl-11-[[2-[(propylmethylamino)methyl]-hexahydro-1H-azepin-1-yl]acetyl]-6H-pyrido[2,3-b][1,4]benzodiazepin-6-one 5,11-dihydro-9-methyl-11-[[2-[[methyl-(1-methylethyl)amino]-methyl]-1-piperidinyl]acetyl]6H-pyrido[2,3-b]1,4]benzodiazepin-6-one The processes according to the invention for obtaining the new condensed diazepinones with basic substituents of the general formula I are as follows:

(a) by reaction of halogenacyl compounds of the general formula II (II)

in which $R^1$, $R^2$, $R^3$ and $R^4$ have the indicated meanings, and Hal is a chlorine, bromine or iodine atom, with secondary amines of the general formula III, (III)

in which $R^5$, $R^6$, A and Z have the meanings defined in the introduction.

The amination is carried out in an inert solvent at temPeratures between $-10°$ C. and the boiling point of the solvent, preferably either with at least 2 moles of secondary amine of the general formula III, or with 1 to 2 moles of a secondary amine of the general formula III and an auxiliary base. Examples of suitable solvents are chlorinated hydrocarbons, such as methylene chloride, chloroform or dichloroethane; open-chain or cyclic ethers, such as diethyl ether, tetrahydrofuran or dioxane; aromatic hydrocarbons, such as benzene, toluene, xylene, chlorobenzene or pyridine; alcohols, such as ethanol or isopropanol; ketones, such as acetone; acetonitrile, dimethyl formamide or 1,3-dimethyl-2-imidazolidinone. Examples of auxiliary bases which may be mentioned are tertiary organic bases such as triethylamine, N-methyl piperidine, diethyl aniline, pyridine and 4-(dimethylamino)pyridine or inorganic bases such as alkali metal or alkaline earth metal carbonates or bicarbonates, hydroxides or oxides. Where appropriate, the reaction rate can be increased by addition of alkali metal iodides. The reaction times depend on the amount and nature of the amine of the general formula III which is used and are between 15 minutes and 80 hours.

(b) By acylation of substituted pyrido[2,3-b][1,4]benzodiazepin-6-ones of the general formula IV, (IV)

in which $R^1$, $R^2$, $R^3$ and $R^4$ have the meanings indicated above, with carboxylic acid derivatives of the general formula V,

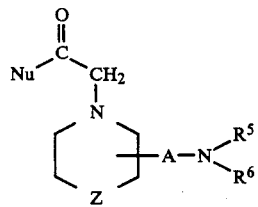

(V)

in which $R^5$, $R^6$, A and Z have the meanings indicated above, and Nu represents a nucleofugal group or leaving group.

The reaction of the compounds of the general formula IV with the acid derivatives of the general formula V is carried out in a manner known per se. The leaving group Nu is a group which forms, together with the carbonyl group to which it is bonded, a reactive carboxylic acid derivative. Examples of reactive carboxylic acid derivatives which may be mentioned are acid halides, esters, anhydrides or mixed anhydrides, as are formed from salts of the corresponding acids (Nu=OH) and acid chlorides, such as phosphorus oxychloride, diphosphoryl tetrachloride or chloroformic esters, or the N-alkyl-2-acyloxypyridinium salts which result from the reaction of compounds of the general formula V (Nu=OH) with N-alkyl-2-halogenopyridinium salts.

The reaction is preferably carried out with the mixed anhydrides of strong mineral acids, in particular of the dichlorophosphoric acid. The reaction is, where appropriate, carried out in the presence of an acid-binding agent (proton acceptor). Examples of suitable proton acceptors which may be mentioned are alkali metal carbonates or bicarbonates, such as sodium carbonate or potassium bicarbonate; tertiary organic amines, such as pyridine, triethylamine, ethyl diisopropylamine, 4-(dimethylamino)pyridine, or sodium hydride. The reaction is carried out at temperatures between −25° C. and 130° C. in an inert solvent. Examples of suitable inert solvents are chlorinated aliphatic hydrocarbons, such as methylene chloride or 1,2-dichloroethane; open-chain or cyclic ethers, such as diethyl ether, tetrahydrofuran or 1,4-dioxane; aromatic hydrocarbons, such as benzene, toluene, xylene or o-dichlorobenzene; polar aprotic solvents such as acetonitrile, dimethylformamide or hexamethylphosphoric triamide; or mixtures thereof. The reaction times depend on the amount and nature of the acylating agent of the general formula V which is used and are between 15 minutes and 80 hours. It is unnecessary to prepare the compounds of the general formula V in pure form; on the contrary, they can be generated in situ in the reaction mixture in a known manner.

Bases of the general formula I which have thus been obtained can then be converted into their acid addition salts, or acid addition salts which have been obtained can be converted into the free bases or other pharmacologically tolerated acid addition salts.

The condensed 6H-pyrido[2,3-b][1,4]benzodiazepin-6-ones with basic substituents, of the general formula I, according to the invention contain up to two independent chiral elements, one of which is an asymmetric carbon atom in the side-chain. The second chiral element is to be regarded as being the acylated tricycle itself, which can exist in two enantiomeric forms. It depends on the nature of the tricycle whether the energy barrier for inversion at this centre is sufficiently high for the individual isomers to be stable and amenable to isolation at room temperature. It has emerged that in compounds of the general formula I which are unsubstituted in the 4-, 7- and 10-positions the required activation energy is so greatly reduced that it is no longer possible to detect diastereomers at room temperature, to say nothing of preparatively isolating them.

The aminoacylated condensed diazepinones of the general formula I, according to the invention, thus contain, as a rule, 2 chiral centres, one of which is, in certain circumstances, not configurationally stable at room temperature. Hence these compounds can occur in two diastereomeric forms or, in each case, as enantiomeric (+) and (−) forms. The invention embraces the individual isomers as well as their mixtures. It is possible to separate the particular diastereomers on the basis of different physicochemical properties, for example by fractional recrystallisation from suitable solvents, by high-pessure liquid chromatography, column chromatoqraphy or gas chromatographic processes.

The resolution of any racemates of the compounds of the general formula I can be carried out by known processes, for example using an optically active acid, such as (+)- or (−)-tartaric acid, or of a derivative thereof, such as (+)- or (−)-diacetyl tartaric acid, monomethyl (+)- or (−)-tartrate or (+)-camphorsulphonic acid.

In a customary process for separating isomers, the racemate of a compound of the general formula I is reacted with one of the above-mentioned optically active acids in equimolar amount in a solvent, and the resulting crystalline diastereomeric salts are separated by utilization of the difference in their solubility. This reaction can be carried out in any type of solvent as long as the difference in the solubility of the salts in the latter is sufficient. It is preferable to use methanol, ethanol, or mixtures thereof, for example in the ratio by volume 50:50. Subsequently each of the diastereomeric salts is dissolved in water, the solution is neutralized with a base, such as sodium carbonate or potassium carbonate, and in this way the corresponding free compound is obtained in the (+)- or (−) form.

In each case only one enantiomer, or a mixture of two optically active diastereomeric compounds covered by the general formula I, is also obtained by carrying out the syntheses which are described above with only one enantiomer of the general formula III or V.

To prepare the halogenoacyl compounds of the general formula II, the starting compounds of the general formula IV are reacted with compounds of the general formula Hal-CH₂CO-Hal' (VII) or [Hal-CH₂-CO]₂O (VIII), in which Hal. has one of the meanings of Hal, and Hal is as defined above. This acylation is carried out without, or preferably in, an inert solvent, at room temperature or elevated temperature, not above the boiling point of the solvent, where appropriate in the presence of an auxiliary base and/or an acylation catalyst. The acid halides of the general formula VII are preferred to the acid anhydrides of the general formula VIII. The preferred acid halide of the general formula VII is chloroacetyl chloride, and the preferred acid anhydride of the general formula VIII is chloroacetic anhydride. Examples of solvents which may be mentioned are aromatic hydrocarbons, such as toluene, xylene or chlorobenzene; open-chain or cyclic ethers, such as diisopropyl ether or dioxane; chlorinated hydrocarbons, such as dichloroethane, and other solvents, such as pyridine, acetonitrile or dimethylformamide.

Examples of auxiliary bases which may be mentioned are tertiary organic bases, such as triethylamine and ethyl diisopropylamine, or pyridine; or inorganic bases, such as anhydrous alkali metal or alkaline earth metal carbonates or bicarbonates or alkaline earth metal oxides. Examples of suitable acylation catalysts are imidazole, pyridine or 4-dimethylaminopyridine.

If Hal in a compound of the general formula II denotes a chlorine atom, it can readily be replaced by the more reactive iodide by reaction with sodium iodide in acetone or ethanol.

Starting compounds of the general formula III in which Z is a methylene group, and $R^5$, $R^6$ and A have the meanings defined in the introduction, are known or can be prepared in analogy to known processes. Thus, for example, those compounds of the general formula III in which A is a methylene group are obtained by reaction of 2- or 3-(chloromethyl)pyridine hydrochloride with a secondary amine of the general formula VI,

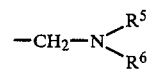
(VI)

in which $R^5$ and $R^6$ are as defined in the introduction (in analogy to A. Fischer et al., Can. J. Chem. 56, 3059–3067 [1967]), followed by catalytic hydrogenation of the resulting tertiary picolylamine, for example in solution in ethanolic hydrochloric acid, and using platinum(IV) oxide as catalyst (see also: F. F. Blicke et al., J. Org. Chemistry 26, 3258 [1961]) or in glacial acetic acid in the presence of platinum(IV) oxide (see also: W. F. Minor et al., J. Med. Pharm. Chem. 5, 96, 105ff [1962]and A. H. Sommers et al., J. Amer. Chem. Soc., 75, 57, 58ff. [1953]).

The 2-[(dialkylamino)methyl]pyrrolidine covered by the diamines of the general formula III, in which Z denotes a single bond, can be obtained by the method of or in analogy to T. Sone et al., Chem. Pharm. Bull. (Tokyo) 21, 2331 [1973]by reduction of appropriate prolinamides with lithium aluminium hydride. If proline is replaced by hexahydro-1H-azepin-2-carboxylic acid in this synthesis (see also H.T. Nagasawa et al., J. Med. Chem. 14, 501 [1971]), then the 2-substituted hexahydro-1H-azepines covered by the general formula III, in which Z represents an ethylene group and A represents a methylene group, and $R^5$ and $R^6$ have the meanings indicated in the introduction, are obtained.

The 3- (dialkylamino)methyl]piperidines covered by the general formula III can also be prepared from corresponding nicotinamides by the method of V. M. Micovic et al., J. Org. Chem. 18, 1196 [1953]or F. Haglid et al., Acta Chem. Scand. 17, 1741 [1963].

3-(Dialkylamino)-pyrrolidines, -piperidines and -hexahydro-1H-azepines (III: $R^5$ and $R^6$ as indicated in the introduction; Z a methylene or ethylene group or a single bond; A a single bond) can be prepared as stated by H. R. Burki et al., Eur. J.Med.Chem. 13, 479–485 [1978]and Smith-Kline Corp., U.S. Pat. No. 3,980,788; C.A. 85, P 182415z [1976] from N-benzyl-3-pyrrolidinone, -3-piperidinone or -hexahydro-1H-azepin-3-one, or in analogy thereto.

3-[(Dialkylamino)methyl]-pyrrolidines in which, in formula III, $R^5$ and $R^6$ are defined as indicated above, Z represents a single bond, and A represents a methylene group in the 3-position, are obtained from the readily accessible 1-benzyl-2,3-dihydro-5(4H)oxo-1H-pyrrol-3-carboxylic acid (Yao-Hua Wu and R. F. Feldkamp, J. Org. Chem. 26, 1519 [1961]) by consecutive reaction with thionyl chloride and an amine of the general formula VI, followed by reduction with lithium aluminium hydride, and removal of the benzyl radical by hydrogenolysis. It is also possible to synthesize 3-[(dialkylamino)methyl]hexahydro-1H-azepines of the formula III in which Z represents a 1,2-ethylene group analogously.

Compounds of the general formula III in which Z is an oxygen atom, and the radical

is located in the 2-position to the secondary amino group, can be obtained, for example, from 4-benzyl-3-(hydroxymethyl)morpholine (G. R. Brown, A. J. Foubister and 8. Wright, J.Chem.Soc. Perkin Trans. I 1985, 2577) by conversion into 4-benzyl-3-(chloromethyl)-morpholine hydrochloride under the action of thionyl chloride, and subsequent reaction with amines of the general formula II and a final elimination of the protective group by hydrogenolysis.

The starting compounds of the general formula IV are known or are prepared by analogy to the processes mentioned in DE-B-3127849.3 and DE-B-1179943.

The starting compounds of the general formula V in which Nu denotes an alkoxy group are obtained by reaction of diamines of the general formula III with halogenoacetic acid esters, where appropriate using additional auxiliary bases, for example triethylamine, or catalysts, for example Triton B. Hydrolysis of the resulting esters, for example with barium hydroxide solution, results in the carboxylic acids covered by the general formula V, which can be used for the preparation of derivatives having other nucleophilic groups.

The invention also relates to medicaments which contain one or more substituted 6H-pyrido[2,3-b][-1,4]benzodiazepin-6-ones of the general formula I, or physiologically tolerated salts thereof.

For this purpose, the compounds of the general formula I can be incorporated in a manner known per se into the customary pharmaceutical formulations, for example into solutions, suppositories, tablets, coated tablets, capsules or infusion preparations. The daily dose is generally between 0.02 and 5 mg/kg, preferably 0.02 and 2.5 mg/kg, in particular 0.05 and 1.0 mg/kg, of body weight, which is, where appropriate, administered in the form of several, preferably 1 to 3, individual doses to achieve the desired results.

The condensed diazepinones of the general formula I, with basic substituents, and their acid addition salts have valuable properties; in particular, they have a favourable effect on the heart rate and, in view of the absence of effects inhibiting gastric acid secretion and inhibiting salivation, and of mydriatic effects, are suitable as vagal pacemakers for the treatment of bradycardia and bradyarrhythmias in human and veterinary medicine; some of the compounds also exhibit spasmolytic properties on peripheral organs, especially the colon and bladder.

A favourable relation between the tachycardiac effects on the one hand, and the undesired effects, which occur with therapeutics with an anticholinergic component of action, on pupil diameter and secretion of tears, saliva and gastric acid on the other hand, is particularly important for the therapeutic use of the substances. The experiments which follow show that the compounds according to the invention have surprisingly favourable relations in this respect.

A. Investigation for functional selectivity of the antimuscarinic effect

Substances with antimuscarinic properties inhibit the effects of exogenous agonists which are administered or f acetylcholine which is released from cholinergic nerve endings. A description of methods suitable for detecting cardioselective antimuscarinics is reproduced hereinafter.

"In vitro" organ preparations

Dissociation constants ($K_B$ values) were determined "in vitro" on the ileum and spontaneously beating atrium of the guinea pig. The ileum was removed and incubated in Krebs-Henseleit solution in an organ bath. Contractions were induced by increasing concentrations of methacholine (M) in such a way that it was possible to construct complete concentration-effect curves. Then M was washed out, the substance to be investigated was added and left in contact for 30 minutes, and again a concentration-effect curve with M was constructed.

The dissociation constant was calculated from the dose ratio (DR), which is the extent of displacement of the concentration-effect curve, by the method of Arunlakshana and Schild (Brit. J. Pharmacol. 14, 48, 1959).

In the isolated, spontaneously beating right atrium, M reduced the heart rate as a function of the concentration. Addition of an antimuscarinic resulted in abolition of this effect. Dissociation constants for the muscarinic receptors of the atrium were obtained in the same way as described above. Comparison of the dissociation constants determined in the two tissues permitted cardioselective substances to be identified. The results are contained in Table Iv.

"In vivo" methods

The methods which were used had the aim of confirming the selectivity of the antimuscarinic effect. Those substances which had been selected on the basis of "in vitro" investigations were examined for their
1. tachycardiac effect on the conscious dog,
2. $M_1/M_2$ selectivity in the rat and
3. effect inhibiting secretion of saliva in the rat.

1. Effect increasing the heart rate in the conscious dog

The substances were either injected intravenously or administered orally, and the heart rate was measured using a tachygraph. After a control period, increasing doses of the compound were administered in order to increase the heart rate. In each case, the next dose was administered when the effect of the preceding dose was no longer evident. The dose of a substance which brought about an increase of 50 beats/min. ($ED_{50}$) was determined graphically. Each substance was examined on 3 to 5 dogs. The results are shown in Table II.

2. $M_1/M_2$ selectivity in the rat

The method which was used has been described by Hammer and Giachetti (Life Sciences 31, 2991–2998 (1982)). Five minutes after intravenous injection of increasing doses of the substance, either the right vagus was electrically stimulated (frequency: 25 Hz; pulse width: 2ms; stimulus duration: 30s; number of volts: supramaximal) or 0.3 mg/kg McN-A-343 was injected intravenously into male THOM rats. The bradycardia induced by stimulation of the vagus, and the increase in blood pressure caused by McN-A-343, were determined. The dose of the substances which reduced either the vagal bradycardia ($M_2$) or the increase in blood pressure ($M_1$) by 50% was determined graphically. See Table III for results.

3. Effect inhibiting secretion of saliva in the rat

As described by Lavy and Mulder (Arch. Int. Pharmacodyn. 178, 437–445, (1969)), male THOM rats which had been anaesthetised with 1.2 g/kg urethane received increasing doses of the substance i.v.. Secretion of saliva was induced by s.c. administration of 2 mg/kg pilocarpine. The saliva was absorbed using blotting paper, and the area covered by it was determined by planimetry every 5 minutes. The dose of the substance which reduced the volume of saliva by 50% was determined graphically. See Table III for results.

B. Studies of binding to muscarinic receptors:

(1) in vitro: Examination of the $IC_{50}$

The organ donors were male Sprague-Dawley rats with a body weight of 180–220 g. After removal of the heart, submandibular gland and cerebral cortex, all further steps were carried out in ice-cold Hepes-HCl buffer (pH 7.4; 100 mmolar NaCl, 10 mmolar $MgCl_2$) The complete heart was cut up with scissors. Finally, all the organs were processed in a potter homogeniser.

The organ homogenates were diluted in the following manner for the binding per se:

| Complete heart | 1:400 |
| Cerebral cortex | 1:3000 |
| Submandibular gland | 1:400 |

The organ homogenates were incubated at a defined concentration of the radio-ligand and a series of concentrations of the non-radioactive test substances in Eppendorf centrifuge tubes at 30° C. The incubation lasted 45 minutes. The radioligand used was 0.3 nmolar $^3$H-N-methylscopolamine ($^3$H-NMS). The incubation was stopped by addition of ice-cold buffer, followed by a vacuum filtration. The filters were washed with cold buffer, and their radioactivity was determined. This represents the total of specific and non-specific binding of $^3$H-NMS. The contribution of the non-specific binding was defined as that radioactivity which was bound in the presence of 1 micromolar quinuclidinyl benzylate.

Determinations were always carried out in quadruplicate. The $IC_{50}$ values of the unlabelled test substances were determined graphically. They represent that concentration of the test substance at which the specific binding of $^3$H-NMS to the muscarinic receptors in the various organs was inhibited by 50%. The results are shown in Table 1.

(2) in vivo: determination of the $ID_{50}$ values

Female rats with a body weight of about 200 g were used for these experiments. Before the start of the experiment, the animals were anaesthetised with a dose of 1.25 g/kg urethane. The animals each received the specified dose of the test substance by i.v. injection. After 15 minutes had elapsed 113 ng/kg $^3$H-N-methylscopolamine ($^3$H-NMS) were administered in the same way. After a further 15 minutes, the animals were sacrificed, and the heart, the bronchi and the lacrimal glands were removed. These organs were dissolved in Soluene R, and the radioactivity was determined. These measurements were assumed to be the total binding. The contribution of non-specific binding was defined as that radioactivity which could not be displaced by a dose of 2 mg/kg atropine. ID$_{50}$ values were determined for the individual organs from these experiments. The ID$_{50}$ values are doses of the test substances which inhibited 50% of the specific binding of $^3$H-NMS to the muscarinic receptors in the particular organs. The results are contained in Table V:

The following compounds, for example, were examined as specified above:

A=9-chloro-11- [[2-[(diethylamino)methyl]-1-piperidinyl]-acetyl]-5,11-dihydro-6H-pyrido[2,3-b]-[1,4]benzodiazepin-6-one and as comparison substances B=11-[[2-[(diethylamino)methyl]-1-piperidinyl]acetyl]-5,11-dihydro-6H-pyrido[2,3-b][1,4]benzodiazepin-6-one (see U.S. Pat. No. 4,550,107)

C=5,11-dihydro-11-[(4-methyl-1-piperazinyl)acetyl]-6H-pyrido[2,3-b][1,4]benzodiazepin-6one (pirenzepine, see U.S. pat. No. 3,660,380)

and

D=atropine.

TABLE I

Receptor binding assay in vitro: Results:

| Substance | Receptor binding assay IC$_{50}$ [nMl$^{-1}$] | | |
|---|---|---|---|
| Submandibular | Cortex | Heart | gland |
| A | 500 | 50 | 1500 |
| B | 1200 | 140 | |
| | 3000 | 150 | 5000 |
| C | 100 | 1500 | 200 |
| D | 2 | 4 | 4 |

TABLE II

Effect increasing the heart rate in the conscious dog: Results:

| Substance | Tachycardia (dog) ED$_{50}$ [microgram/kg] | | Ratio |
|---|---|---|---|
| p.o./ED$_{50}$ i.v. | intravenous | oral | ED$_{50}$ |
| A | 170 | 380 | 2 |
| B | 120 | 1750 | 15 |

TABLE III

M$_1$/M$_2$ selectivity and effect inhibiting the secretion of saliva in the rat: Results:

| Substance | M$_2$-activity (rat) ED$_{50}$ [microgram/kg] i.v. | M$_1$-activity (rat) ED$_{50}$ [microgram/kg] i.v. | Inhibition of secretion of saliva (rat) ED$_{50}$ [microgram/kg] i.v. |
|---|---|---|---|
| A | 77 | 1476 | 7568 |
| B | 160 | 988 | 4215 |
| C | 883 | 40 | 84 |
| D | 4 | 16 | 9 |

TABLE IV

Dissociation constants (K$_B$ values) on the ileum and spontaneously beating atrium of the guinea pig: Results:

| Substance | K$_B$ [mol/l] | |
|---|---|---|
| | Heart | Ileum |
| A | 1.48 × 10$^{-8}$ | 5.13 × 10$^{-7}$ |
| B | 1.05 × 10$^{-7}$ | 6.17 × 10$^{-7}$ |
| C | 2.4 × 10$^{-7}$ | 1.55 × 10$^{-7}$ |
| D | 1.41 × 10$^{-9}$ | 8.13 × 10$^{-10}$ |

TABLE V

Receptor binding assay in vivo: Results:

| Substance | ID$_{50}$ [mg/kg] | | | |
|---|---|---|---|---|
| | Heart | | Bronchi | Lacrimal gland |
| | Atrium | Ventricle | | |
| A | 0.6 | 0.3 | 8.0 | 30.0 |
| B | 1.0 | 0.6 | 15.0 | 30.0 |
| C | 5.0 | 1.0 | 10.0 | 10.0 |
| D | 0.08 | 0.03 | 0.1 | 0.2 |

The data in Table I above demonstrate that the new compounds of the general formula I distinguish between muscarinic receptors in different tissues.

This follows from the considerably lower IC$_{50}$ values on investigation of products from the heart compared with those from the cerebral cortex and submandibular gland.

It is evident from the pharmacological data in Table III above, in full agreement with the receptor binding studies, that the heart rate is increased by the said compounds even at doses of which no curtailment of secretion of saliva is yet observed.

In addition, the pharmacological data in Table IV above indicate that the ability to distinguish between heart and smooth muscle is surprisingly large. The absorption of the said compounds is excellent because, as is evident from Table II, they are almost as effective after oral administration as after intraveous injection.

Table V shows the preferred binding to receptors in the heart (atrium/ventricle).

In addition, the compounds prepared according to the invention are well tolerated, and thus no toxic side effects were observed even with the highest doses administered in the pharmacological investigations.

The Examples which follow are intended to illustrate the invention in detail:

"M.p." denotes "melting point", "D." denotes "decomposition". Satisfactory elemental analyses and IR, UV, $^1$H NMR and, frequently, mass spectra are available for all the compounds.

PREPARATION OF THE STARTING MATERIALS

Example A

2-Chloro-11-(chloroacetyl)-5,11-dihydro-6H-pyrido[2,3b][1,4]benzodiazepin-6-one 9.08 g (0.04 mole) of 5,11-dihydro-6H-pyrido[2,3-b][1,4]benzodiazepin-6-on-1-oxide (CRC Compagnia di Ricerca Chimica S.p.A., S. Giovanni al Natisone DE-A-3208656) were suspended in 150 ml of dry acetonitrile and, after addition of 42.6 g (0.37 mole) of chloroacetyl chloride, the mixture was heated at an internal temperature of 76° C for 2 hours. It was then cooled to 0° C., left to stand at this temperature for 2 hours, and the resulting precipitate was filtered off with suction and washed with 50 ml of cold acetonitrile. The mother liquor was evaporated in vacuo, the oily residue was thoroughly triturated with a mixture of 20 ml of acetonitrile and 50 ml of water, and the crystalline precipitate was filtered off with suction and washed with 100 ml of water. The two fractions were combined and dried at 40° C. in vacuo. Yield: 11.64 g (90% of theory). Recrystallisation from ethanol was used for Purification. Colourless crystals of m.p. 235–238° C. (D.).

Example B

9-Chloro-11-(chloroacetyl)-5,11-dihydro-6H-pyrido[2,3b][1,4]benzodiazepin-6-one 40 ml (0.529 mole) of chloroacetyl chloride were added dropwise, within 30 minutes, to a boiling mixture of 81.7 g (0.333 mole) of 9-chloro-5,11-dihydro-6H-pyrido[2,3-b][1,4]benzodiazepin-6-one, 1660 ml of anhydrous dioxane and 75 ml (0.536 mole) of triethylamine, and the mixture was then stirred at the reflux temperature for 4 hours. The mixture was filtered while still hot, and the residue on the filter was thoroughly washed with ice-cold water and combined with the product which had been obtained by concentration of the dioxane-containing filtrate and trituration of the residue with water. Drying in vacuo was followed by crystallisation from dimethyl formamide. Colourless crystals of m.p. 228–230° C. Yield: 96 g (89% of theory).

The following were obtained correspondingly:

11-(chloroacetyl)-5,11-dihydro-2-methyl-6H-pyrido[2,3-b][1,4]benzodiazepin-6-one of m.p. 202–204° C. (D.) (from xylene);

8-chloro-11-(chloroacetyl)-5,11-dihydro-6H-pyrido[2,3-b][1,4]benzodiazepin-6-one of m.p. 211–212° C. (D.) (frm ethanol);

11-(chloroacetyl)-5,11-dihydro-8-methyl-6H-pyrido[2,3-b][1,4]benzodiazepin-6-one of m.p. 233–235° C. (from ethoxyethanol);

11-(chloroacetyl)-5,11-dihydro-2,4,10-trimethyl-6H-pyrido[2,3-b][1,4]benzodiazepin-6-one of m.p. 151–153° C. (acetonitrile);

11-(chloroacetyl)-5,11-dihydro-2,4-dimethyl-6H-pyrido[2,3-b][1,4]benzodiazepin-6-one of m.p. 194–195° C. (D.) (acetonitrile);

11-(chloroacetyl)-5,11-dihydro-2,10-dimethyl-6H-pyrido[2,3-b][1,4]benzodiazepin-6-one of m.p. 230–232° C. (D.) (isopropanol);

11-(chloroacetyl)-5,11-dihydro-10-methyl-6H-pyrido[2,3-b][1,4]benzodiazepin-6-one of m.p. 219–220° C. (from acetonitrile);

11-(chloroacetyl)-5,11-dihydro-2,8-dimethyl-6H-pyrido[2,3-b][1,4]benzodiazepin-6-one;

11-(chloroacetyl)-2,9-dichloro-5,11-dihydro-6H-pyrido[2,3-b][1,4]benzodiazepin-6-one;

11-(chloroacetyl)-5,11-dihydro-8,9-dimethyl-6H-pyrido[2,3-b][1,4]benzodiazepin-6-one;

11-(chloroacetyl)-5,11-dihydro-8-ethyl-6H-pyrido[2,3-b][1,4]benzodiazepin-6-one of m.p. 200° to 201° C.;

11-(chloroacetyl)-5,11-dihydro-9-methyl-6H-pyrido[2,3-b][1,4]benzodiazepin-6-one of m.p. 205° C. (D.);

8-bromo-11-(chloroacetyl)-5,11-dihydro-6H-pyrido[2,3-b][1,4]benzodiazepin-6-one of m.p. 222° C. (D.);

9-bromo-11-(chloroacetyl)-5,11-dihydro-6H-pyrido[2,3-b][1,4]benzodiazepin-6-one;

11-(chloroacetyl)-5,11-dihydro-7-fluoro-6H-pyrido[2,3-b][1,4]benzodiazepin-6-one;

11-(chloroacetyl)-5,11-dihydro-8-fluoro-6H-pyrido[2,3-b][1,4]benzodiazepin-6-one;

11-(chloroacetyl)-5,11-dihydro-9-fluoro-6H-pyrido[2,3-b][1,4]benzodiazepin-6-one;

11-(chloroacetyl)-5,11-dihydro-2,4,8-trimethyl-6H-pyrido[2,3-b][1,4]benzodiazepin-6-one of m.p. 230° C. (isopropanol).

Example C

3-[(Diethylamino)methyl]pyrrolidine 9.43 ml (0.131 mole) of thionyl chloride was added to a suspension of 26.0 g (0.119 mole) of 1-benzyl-2,3-dihydro-5(4H)-oxo-1H-pyrrol-3-carboxylic acid in 200 ml of anhydrous tetrahydrofuran, and the mixture was maintained at 45° C., with stirring, for 1 hour. The resulting clear solution was evaporated in vacuo, the residue was taken up in 200 ml of fresh tetrahydrofuran, and a solution of 36.5 ml (0.355 mole) of diethylamine in 200 ml of dry tetrahydrofuran was added dropwise. The mixture was boiled under reflux for 3 hours and then, after cooling, the precipitated diethylamine hydrochloride was removed. The filtrate was evaporated, and the remaining oil was taken up in 200 ml of a mixture of 2 parts of diethyl ether and 1 part of ethyl acetate, and the solution was treated with 3 g of active charcoal and again evaporated. The remaining viscous, yellowish product (30.0 g, 92% of theory) was, without further purification, taken up in 500 ml of anhydrous tetrahydrofuran, and the solution was added dropwise to a suspension of 8.36 q 0.22 mole) of lithium aluminium hydride in 500 ml of tetrahydrofuran. The mixture was then boiled under reflux for 2 hours, allowed to cool, and 9 ml of water, 9 ml of 15% aqueous sodium hydroxide solution and 27 ml of water were added successively. The mixture was filtered, and the filtrate was evaporated in vacuo. The resulting oily residue (25 g, 93% of theory) was dissolved in 100 ml of ether and converted into the hydrochloride. The solution of this hydrochloride in 350 ml of methanol was hydrogenated in the presence of 12 g of 10% palladium/animal charcoal at room temperature and under atmospheric pressure until hydrogen uptake was complete. The usual working up was carried out and 12.5 g (79% of theory; overall yield: 67% of theory) of a colourless oil resulted, boiling point 88–93° C. (12 mm Hg).

Example D

3-[(Diethylamino)methyl]morpholine 20.2 g (0.17 mole) of thionyl chloride were added dropwise to a solution of 16.6 g (0.08 mole) of 4-benzyl-3-(hydroxymethyl)morpholine in 100 ml of anhydrous dichloromethane, during which the temperature of the mixture spontaneously increased. It was then boiled under reflux for 2 hours, and the resulting deep brown mixture was cooled and then stirred with 100 ml of toluene, and the mixture was concentrated in vacuo. The residue was triturated with 10 ml of a toluene/acetonitrile mixture (1:1 v/v), by which means 18.0 g (86% of theory) of colourless, very hygroscopic crystals (4-benzyl-3-(chloromethyl)morpholine hydrochloride) were obtained, and these were dissolved in 30 ml of ethanol ahd, after addition of 73.14 g (1.0 mole) of diethylamine and 1.5 g of sodium iodide, the mixture was heated in an autoclave at 100° C. for 6 hours. The mixture was allowed to cool, evaporated in vacuo, and the remaining residue was digested with 100 ml of hot t-butyl methyl ether. The mixture was filtered, and the filtrate was treated with 1 g of animal charcoal, boiled and filtered again. The oily residue remaining after evaporation was purified by column chromatography on 600 g of silica gel (Macherey-Nagel, 35–70 mesh) using dichloromethane/ethyl acetate/cyclohexane/methanol concentrated ammonia 52.8/41.7/2.6/2.6/0.3 (v/v). The fraction with $R_F$ 0.6 (Macherey-Nagel, Polygram ® Sil G/UV$_{254}$ precoated plastic sheets for TLC, mobile Phase as above) was isolated and identified by spectroscopy and elemental analysis as the 4-benzyl-3-[(diethylamino)methyl]morpholine which was sought. Yield: 15.3 g (85% of theory). The colourless compound was dissolved in 230 ml of ethanol and, after addition of 3 g of palladium hydroxide, was hydrogenated for 30 minutes under a pressure of 5 bar of hydrogen. After removal of the catalyst and the usual working up, 7.0 g (70% of theory) of a colourless oil of boiling point (12) 98–110° C. (Kugelrohr) were obtained. Overall yield over all the steps: 51% of theory.

Example E

2-[(Dipropylamino)methyl]piperidine

A mixture of 170.1 g (1.0 mole) of 2-(chloromethyl)-piperidine hydrochloride (M. Rink and H. G. Liem, Arch. Pharm. 292, 165–169 (1959)), 506 g (5.0 moles) of dipropylamine and 1.7 l of dichloromethane were boiled under reflux for 3 hours, then evaporated in vacuo, and the residue was made alkaline with potassium hydroxide solution with external ice cooling. Exhaustive extraction with t-butyl methyl ether was carried out, and the combined extracts were washed twice with 100 ml of water each time, dried over sodium sulphate, and the solvent was removed by distillation in vacuo. The residue was fractionally distilled under water pump vacuum. Colourless oil of boiling point 108–114° C. (12 mm Hg). Yield: 108.6 g (55% of theory).

Example F

9-Chloro-5,11-dihydro-6H-pyrido[2,3-b][1,4]benzodiazepin-6-one 139.0 g (1.24 mole) of potassium tert.-butanolate were added to a solution of 144.0 g (1.12 mole) of 2-chloro-3-pyridinamine in 432 ml of dry dimethyl sulphoxide, and the mixture was stirred at a reaction temperature of 40° C. for 10 minutes. A solution of 207.0 g (1.12 mole) of methyl 2-amino-4-chlorobenzoate in 250 ml of dimethyl sulphoxide was added dropwise to the resulting dark solution, and the mixture was then heated at 50° C. for 30 minutes. It was allowed to cool, stirred into 1 liter of ice-water, and the pH was adjusted to 4 by addition of 20% aqueous hydrochloric acid. The resulting mass of crystals was filtered off with suction, then suspended in 1 litre of 1% aqueous ammonia, and again filtered with suction. After drying in a circulating air dryer: colourless crystals of m.p. 189 192° C., which were immediately reacted further without further purification. $R_F$ 0.8 (Macherey-Nagel, Polygram ® SIL G/UV$_{254}$ precoated plastic sheets for TLC, mobile phase: ethyl acetate/dichloromethane 1:1 v/v).

Yield 2253 g (80% of theory).

278.3 g (0.986 mole) of the resulting 2-amino-4-chloro-N-(2-chloro-3-pyridinyl)benzamide were suspended in 436 ml of anhydrous 1,2,4-trichlorobenzene and, while stirring, heated at 220° C. for 8 hours and then at 250° C. for 8 hours. The mass of crystals obtained after cooling was filtered off with suction and thoroughly washed twice with 50 ml of trichlorobenzene each time, then with 100 ml of dichloromethane and finally with 100 ml of a mixture of 50 ml of ethanol and 50 ml of concentrated ammonia. The product was recrystallised from 250 ml of boiling dimethyl formamide, and the resulting crystals were then washed twice with 50 ml of dimethyl formamide and of methanol each time, and dried in a circulating air dryer. Yield: 8.4 g of pale yellow crystals, m.p. 360° C., $R_F$ 0.70 (Macherey-Nagel, Polygram ® SIL G/UV$_{254}$, pre-coated plastic sheets for TLC, mobile phase: ethyl acetate/dichloromethane/petroleum ether 42:42:16 v/v). A further 17.5 g of material of the same quality could be obtained from the mother liquors by evaporation and working up in the same way. Overall yield: 101.5 g (41.3% of theoy).

The following were obtained correspondingly:

5,11-dihydro-2-methyl-6H-pyrido[2,3-b][1,4]benzodiazepin-6-one of m.p. 257–259° C. (DMF);

8-chloro-5,11-dihydro-6H-pyrido[2,3-b][1,4]benzodiazepin-6-one of m.p. 307–309° C. (DMF);

5,11-dihydro-8-methyl-6H-pyrido[2,3-b]1,4]benzodiazepin-6-one of m.p. 257–258° C. (diethylene glycol diethyl ether);

5,11-dihydro-2,4,10-trimethyl-6H-pyrido[2,3-b][1,4]benzodiazepin-6-one of m.p. 310–313° C. (ethylene glycol);

5,11-dihydro-2,4-dimethyl-6H-pyrido[2,3-b][1,4]benzodiazepin-6-one of m.p. 281–283° C. (from N,N-dimethylacetamide);

5,11-dihydro-2,10-dimethyl-6H-pyrido[2,3-b][1,4]benzodiazepin-6-one of m.p. 251–253° C. (xylene);

5,11-dihydro-10-methyl-6H-pyrido[2,3-b][1,4]benzodiazepin-6-one of m.p. 226–228° C. (xylene);

5,11-dihydro-2,8-dimethy1-6H-pyrido[2,3-b][1,4]benzodiazepin-6-one of m.p. 244–246° C. (xylene)

2,9-dichloro-5,11-dihydro-6H-pyrido[2,3-b][1,4]benzodiazepin-6-one of m.p. 310° C.;

5,11-dihydro-8,9-dimethyl-6H-pyrido[2,3-b][1,4]benzodiazepin-6-one;

5,11-dihydro-8-ethyl-6H-pyrido[2,3-b][1,4]benzodiazepin-6-one of m.p. 232° to 234° C. (from 70% by weight aqueous acetic acid);

5,11-dihydro-9-methyl-6H-pyrido[2,3-b][1,4]benzodiazepin-6-one of m.p. 286° to 288° C.;

8-bromo-5,11-dihydro-6H-pyrido[2,3-b][1,4]benzodiazepin-6-one of m.p. 338° to 340° C. (acetonitrile);

9-bromo-5,11-dihydro-6H-pyrido[2,3-b][1,4]benzodiazepin-6-one;

5,11-dihydro-7-fluoro-6H-pyrido[2,3-b][1,4]benzodiazepin-6-one;

5,11-dihydro-8-fluoro-6H-pyrido[2,3-b][1,4]benzodiazepin-6-one;

5,11-dihydro-9-fluoro-6H-pyrido[2,3-b][1,4]benzodiazepin-6-one of m.p. 330° C. (D.);

10-chloro-5,11-dihydro-6H-pyrido[2,3-b][1,4]benzodiazepin-6-one of m.p. 303–305° C. (N,N-dimethylacetamide);

2-chloro-5,11-dihydro-6H-pyrido[2,3-b][1,4]benzodiazepin-6-one of m.p. 276–278° C. (n-propanol);

5,11-dihydro-2,4%8-trimethyl-6H-pyrido[2,3-b][1,4]benzodiazepin-6-one of m.p. 228–230° C. (xylene).

Preparation of the final products:

Example 1

2-Chloro-11-[[2-[(diethylamino)methyl]-1-piperidinyl]acetyl]-5,11-dihydro-6H-pyrido[2,3-b][1,4]benzodiazepin-6-one A mixture of 7.1 g (0.22 mole) of 2-chloro-11-(chloroacetyl)-5,11-dihydro-6H-pyrido[2,3-b][1,4]benzodiazepin-6-one, 30 ml of anhydrous dimethyl formamide, 4.4 g (0.0258 mole) of D,L-2[-(diethylamino)methyl]piperidine and 2.4 g (0.0226 mole) of sodium carbonate was stirred at a reaction temperature of 60° C. for 1 hour and of 70° C. for 2 hours. The cooled reaction mixture was stirred into 300 ml of ice-water, and the colourless precipitate which separated out was filtered off with suction and recrystallised from 50 ml of ethanol, using 0.5 g of animal charcoal. 6.2 g (62% of theory) of colourless crystals of m.p. 191–192.5° C. were obtained.

Example 2

9-Chloro-11-[[2-[(diethylamino)methyl]-1-piperidinyl]acetyl]-5,11-dihydro-6H-pyrido[2,3-b][1,4]benzodiazepin-6-one A mixture of 125 g (0.388 mole) of 9-chloro-11-(chloroacetyl)-5,11-dihydro-6H-pyrido[2,3-b][1,4]-benzodiazepin-6-one, 2480 ml of dry dimethyl formamide, 73.0 g (0.429 mole) of D,L-2-[(diethylamino)methyl]-piperidine, 60 ml (0.429 mole) of anhydrous triethylamine and 3.0 g of sodium iodide was stirred at an internal temperature of 50° C. for 32 hours and then at room temperature for 15 hours. Insolubles were removed by filtration, and the filtrate was evaporated at the oil pump and at a bath temperature of 45° C. The remaining product was dissolved in 5% hydrochloric acid, and the solution was extracted by shaking twice with 50 ml of dichloromethane each time. The aqueous layer was made alkaline by addition of concentrated potassium carbonate solution, and the liberated base was taken up in dichloromethane, and the solution was treated with 2 g of active charcoal and dried over sodium sulphate. The dark oil remaining after the solvent had been removed by evaporation was purified by column chromatography on 800 g of silica gel (35–70 mesh) using dichloro- methane/methanol/ethyl acetate/cyclohexane/concentrated ammonia 59/7.5/25/7.5/1 (v/v) for elution. The fractions containing the compound which was sought (132 g) were dissolved in dilute aqueous maleic acid solution. The filtered solution was washed four times with 50 ml of ethyl acetate each time, and was then saturated with solid potassium carbonate and exhaustively extracted with dichloromethane. The combined dichloromethane phases were dried over sodium sulphate and evaporated, and 109 g of a partially crystallised oil remained. After recrystallisation twice from 450 ml of acetonitrile each time, using 2 g of active charcoal each time, 63.0 g (36% of theory) of colourless crystals of m.p. 167.5–169° C. were obtained.

Example 3

11-[[2-[(Diethylamino)methyl]-1-piperidinyl]acetyl]5,11-dihydro-8-methyl-6H-pyrido[2,3-b][1,4]benzodiazepin-6-one Prepared in analogy to Example 2 from 11-(chloroacetyl)-5,11-dihydro-8-methyl-6H-pyrido[2,3-b][1,4]benzodiazepin-6-one and 2-[(diethylamino)methyl]piperidine, but using acetonitrile as solvent, in a yield of 54% of theory. M.p. 173–174° C. (diisopropylether).

Example 4

11-[[2-[(Diethylamino)methyl]-1-piperidinyl]acetyl]5,11-dihydro-2-methyl-6H-pyrido[2,3-b][1,4]benzodiazepin-6-one Prepared by analogy to Example 2 from 11-(chloroacetyl)-5,11-dihydro-2-methyl-6H-pyrido[2,3-b][1,4]benzodiazepin-6-one and 2-[(diethylamino)methyl]piperidine, but using acetonitrile as solvent, in a yield of 65% of theory. M.p. 184–186° C. (after recrystallisation from diisopropyl ether and acetonitrile, in each case using active charcoal).

The following were obtained correspondingly: 11-[[2-[(Diethylamino)methyl]-1-piperidinyl]acetyl]-5,11-dihydro-9-methyl-6H-pyrido[2,3-b][1,4]benzodiazepin-6-one of m.p. 172° to 174° C. (acetonitrile);

8-Chloro-11-[[2-[(diethylamino)methyl]-1-piperidinyl]acetyl]-5,11-dihydro-6H-pyrido[2,3-b][1,4]benzodiazepin-6-one of m.p. 186° to 188° C. (acetonitrile using active charcoal);

11-[[2-[(Diethylamino)methyl]-1-piperidinyl]acetyl]5,11-dihydro-2,4,10-trimethyl-6H-pyrido[2,3-b][1,4]benzodiazepin-6-one;

11-[[2-[(Diethylamino)methyl]-1-piperidinyl]acetyl]5,11-dihydro-2,4,8-trimethyl-6H-pyrido[2,3-b][1,4]benzodiazepin-6-one of m.p. 213° to 215° C. (acetonitrile);

11-[[2-[(Diethylamino)methyl]-1-Piperidinyl]acetyl]5,11-dihydro-2,8-dimethyl-6H-pyrido[2,3-b][1,4]benzodiazepin-6-one;

2,9-Dichloro-11-[[2-[(diethylamino)methyl]-1-piperinyl]-acetyl]-5,11-dihydro-6H-pyrido[2,3-b][1,4]benzodiazepin-6-one;

11-[[2-[(Diethylamino)methyl]-1-piperidinyl]acetyl]5,11-dihydro-8-fluoro-6H-pyrido[2,3-b][1,4]benzodiazepin-6-one;

11-[[2-[(Diethylamino)methyl]-1-piperidinyl]acetyl]5,11-dihydro-9-fluoro-6H-pyrido[2,3-b][1,4]benzodiazepin-6-one;

11-[[2-[(Diethylamino)methyl]-1-piperidinyl]acetyl]5,11-dihydro-7-fluoro-6H-pyrido[2,3-b][1,4]benzodiazepin-6-one;

8-Bromo-11-[[2-[(diethylamino)methyl]-1-piperidinyl]acetyl]-5,11-dihydro-6H-pyrido[2,3-b][1,4]benzodiazepin-6-one of m.p. 165° to 167° C. (acetonitrile using active charcoal);

11-[[2-[(Diethylamino)methyl]-1-piperidinyl]acetyl]5,11-dihydro-8-ethyl-6H-pyrido[2,3-b][1,4]benzodiazepin-6-one of m.p. 141° to 143° C. (diisopropyl ether);

(+)-9-Chloro-11-[[2-[(diethylamino)methyl]-1-piperidinyl]-acetyl]-5,11-dihydro-6H-pyrido[2,3-b][1,4]benzodiazepin-6-one;

(-)-9-Chloro-11-[[2-[(diethylamino)methyl]-1-piperidinyl]-acetyl]-5,11-dihydro-6H-pyrido[2,3-b][1,4]benzodiazepin-6-one;

9-Chloro-5,11-dihydro-11-[[2-[(dimethylamino)methyl]-1piperidinyl]acetyl]-6H-pyrido[2,3-b][1,4]benzodiazepin6-one;

9-Chloro-5,11-dihydro-11-[[2-[(1-pyrrolidinyl)methyl]1-piperidinyl]acetyl]-6H-pyrido[2,3-b][1,4]benzodiazepin-6-one;

9-Chloro-5,11-dihydro-11-[[2-[(4-morpholinyl)methyl]-1piperidinyl]acetyl]-6H-pyrido[2,3-b][1,4]benzodiazepin-6-one;

9-Chloro-11-[[3-[(diethylamino)methyl]-1-piperidinyl]acetyl]-5,11-dihydro-6H-pyrido[2,3-b][1,4]benzodiazepin-6-one;

(S)-9-Chloro-11-[[2-[(diethylamino)methyl]-1-pyrrolidinyl]-acetyl]-5,11-dihydro-6H-pyrido[2,3-b][1,4]benzodiazepin-6-one;

9-Chloro-5,11-dihydro-11-[[3-(dimethylamino)-1-piperidinyl]-acetyl]-6H-pyrido[2,3-b][1,4]benzodiazepin-6one;

D,L-9-Chloro-11-[[3-[(diethylamino)methyl]-4-morpholinyl]-acetyl]-5,11-dihydro-6H-pyrido[2,3-b][1,4]benzodiazepin-6-one.

Example 5

9-Chloro-11-[[2-[(diethylamino)methyl]-1-piperidinyl]acetyl]-5,11-dihydro-6H-pyrido[2,3-b][1,4]benzodiazepin-6-one 5.6 g (0.0174 mole) of 9-chloro-11-(chloroacetyl)-5,11-dihydro-6H-pyrido[2,3-b][1,4]benzodiazepin-6-one were suspended in 100 ml of anhydrous dioxane and, after addition of 6.0 g (0.035 mol) of 2-[(diethylamino)-methyl]piperidine, the mixture was boiled under reflux for 12 hours.

The mixture was evaporated, and the residue was then treated as in Example 2. 2.1 g (26% of theory) of colourless crystals of m.p. 167.5–169° C. (acetonitrile/active charcoal) were obtained.

Example 6

9-Chloro-11-[[2-[(diethylamino)methyl]-1-piperidinyl]acetyl]-5,11-dihydro-6H-pyrido[2,3-b][1,4]benzodiazepin-6-one A mixture of 14.43 g (0.0632 mole) of 2-[(diethylamino)-methyl]-1-piperidine acetic acid and 2.0 g of a 75% sodium hydride dispersion in liquid paraffin in 160 ml of dimethyl formamide was heated at 50° to 80° C. until evolution of hydrogen had stopped. 15.35 g (0.0625 mole) of 9-chloro-5,11-dihydro-6H-pyrido[2,3-b][1,4]benzodiazepin-6-one were added to the resulting sodium salt of the said acid, and, at −10° C., 9.9 g (0.0646 mole) of phosphorus oxychloride were added dropwise within 10 minutes. The mixture was stirred at −10° C. for 4 hours, at 0° C. for 4 hours and at room temperature for 20 hours. The mixture was stirred into 300 g of ice, the pH was adjusted to 9 with sodium hydroxide solution, and the mixture was exhaustively extracted with dichloromethane. The combined organic phases were washed once with a little ice-water, dried over sodium sulphate and evaporated. The residue was recrystallised from acetonitrile using active charcoal. Colourless crystals of m.p. 167.5–169° C., according to the thin-layer chromatogram, mixed melting point, IR, UV and $^1$H NMR spectrum completely identical to a sample were obtained as in Example 2. Yield: 5.1 g (18% of theory).

The preparation of pharmaceutical use forms is described hereinafter by means of some Examples:

Example I

Tablets containing 5 mg of 9-chloro-11-[[2-[(diethylamino)methyl]-1-piperidinyl]acetyl]-5,11-dihydro-6H-pyrido[2,3-b][1,4]benzodiazepin-6-one Composition

| 1 tablet contains: | |
|---|---|
| Active compound | 5.0 mg |
| Lactose | 148.0 mg |
| Potato starch | 65.0 mg |
| Magnesium stearate | 2.0 mg |
| | 220.0 mg |

Preparation process

A 10% strength mucilage is prepared from potato starch by heating. The active substance, lactose and the remaining potato starch are mixed and granulated with the above mucilage through a screen of mesh width 1.5 mm. The granules are dried at 45° C., rubbed once more through the above screen, mixed with magnesium stearate and compressed to form tablets.

| Tablet weight: | 220 mg |
|---|---|
| Punch: | 9 mm |

Example II

Coated tablets containing 5 mg of 9-chloro11-[[2-[(diethylamino)methyl]-1-piperidinyl]acetyl]5,11-dihydro-6H-pyrido[2,3-b][1,4]benzodiazepin-6-one The tablets prepared as in Example I are covered, by a known process, with a coating which essentially consists of sugar and talc. The finished coated tablets are polished with beeswax.

Coated tablet weight: 300 mg

Example III

Ampoules containing 10 mg of 9-chloro-11-[[2[(diethylamino)methyl]-1-piperidinyl]acetyl]-5,11-dihydro-6H-pyrido[2,3-b][1,4]benzodiazeoin-6-one Composition

| 1 ampoule contains: | |
|---|---|
| Active compound | 10.0 mg |
| Sodium chloride | 8.0 mg |
| Distilled water ad | 1 ml |

Preparation process

The active subtance and sodium chloride are dissolved in distilled water and then made up to the stated volume. The solution is sterilised by filtration and dispensed into 1 ml ampoules.

Sterilisation: 20 minutes at 120° C.

Example IV

Suppositories containing 20 mq of 9-chloro-11[[2-[(diethylamino)-methyl]-1-piperidinyl]acetyl]-5,11-dihydro-6H-pyrido[2,3-b][1,4]benzodiazepin-6-one Composition

| 1 suppository contains: | |
|---|---|
| Active compound | 20.0 mg |
| Suppository base (for example Witepsol W 45$^{(R)}$) | 1 680.0 mg |

-continued

| 1 suppository contains: | |
|---|---|
| | 1 700.0 mg |

Preparation process

The finely powdered active substance is suspended in the suppository base which has been melted and cooled to 40° C. The composition is cast at 37° C. in suppository moulds which have been slightly pre-cooled.

Suppository weight 1.7 g

Example V

Drops containing 4,9-dihydro-9-chloro-11-[[2-[(diethylamino)-methyl]-1-piperidinyl]acetyl]-5,11-dihydro-6H-pyrido[2,3-b][1,4]benzodiazepin-6-one

Composition 100 ml of drops solution contain:

| Methyl p-hydroxybenzoate | 0.035 | g |
|---|---|---|
| Propyl p-hydroxybenzoate | 0.015 | g |
| Aniseed oil | 0.05 | g |
| Menthol | 0.06 | g |
| Pure Ethanol | 10.0 | g |
| Active compound | 0.5 | g |
| Sodium cyclamate | 1.0 | g |
| Glycerol | 15.0 | g |
| Distilled water ad | 100.0 | ml |

Preparation process

The active substance and sodium cyclamate are dissolved in about 70 ml of water, and glycerol is added. The p-hydroxybenzoates, aniseed oil and menthol are dissolved in ethanol, and this solution is added to the stirred aqueous solution. Finally, the mixture is made up to 100 ml with water, and is filtered to remove suspended particles.

We claim:

1. A compound selected from the compounds of formula I

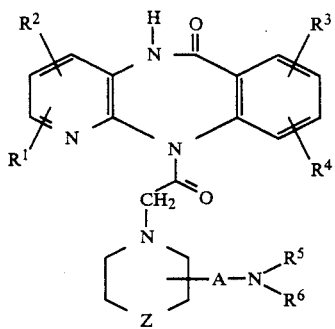

in which $R^1$ is $C_1$–$C_4$ alkyl, chloro or hydrogen;

$R^2$ is hydrogen or methyl;

$R^3$ and $R^4$ each are hydrogen, fluoro, chloro, bromo, or $C_1$–$C_4$ alkyl;

$R^5$ and $R^6$ are $C_1$–$C_6$ alkyl, or form, together with the nitrogen atom between them, a 5- to 7-membered saturated, monocyclic, heteroaliphatic ring, a 6-membered ring being optionally interrupted by an oxygen atom or by a N—$CH_3$ group in the 4-position;

Z is a single bond, oxygen, methylene or 1,2-ethylene group; and

A is methylene in the 2- or 3- position of the heteroaliphatic ring

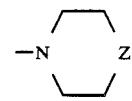

and, in the case of linkage to the 3- position, A can also denote a direct bond, with the proviso that at least one of the radicals $R^1$, $R^2$, $R^3$, and $R^4$ is different from hydrogen, and physiologically tolerated salts thereof with inorganic or organic acids.

2. The compound as recited in claim 1, in which
   $R^1$ is chloro or methyl,
   $R^2$ is hydrogen or methyl,
   $R^3$ is hydrogen, chloro or ethyl,
   $R^4$ is hydrogen,
   $R^5$ or $R^6$ are methyl or ethyl, and
   A and Z are methylene,
   and physiologically tolerated salts thereof with inorganic or organic acids.

3. The compound as recited in claim 1, in which $R^1$, $R^2$ and $R^3$ are hydrogen,
   $R^4$ is bromo or ethyl,
   $R^5$ and $R^6$ are methyl or ethyl,
   A and Z are methylene
   and physiologically tolerated salts thereof with inorganic or organic acids 4. 9-Chloro-11-[[2-[(diethylamino)methyl]-1-piperidinyl]acetyl]-5,11-dihydro-6H-pyrido[2,3-b][1,4]benzodiazepin-6-one and physiologically tolerated salts thereof with inorganic or organic acids.

5. A pharmaceutical composition of matter comprising a therapeutically effective amount of a compound as recited in claim 1 and a pharmaceutically acceptable carrier.

6. A method for treatment of bradycardia in a warm-blooded animal which comprises administering a therapeutically effective amount to said animal of a compound as recited in claim 1.

7. A method for treatment of bradyarrhythmia in a warm-blooded animal which comprises administering a therapeutically effective amount to said animal of a compound as recited in claim 1.

* * * * *